United States Patent
Uh et al.

(10) Patent No.: US 6,515,157 B2
(45) Date of Patent: Feb. 4, 2003

(54) FERROCENYLDIPHOSPHINE-RUTHENIUM COMPLEXES AND A HYDROGENATION PROCESS OF EXOCYCLIC DOUBLE BOND OF D-THIOPHENE TO D-THIOPHANE

(76) Inventors: Hong-Sun Uh, #104-902, Pooleunmaeul APT., 719 Ilwonbon-dong, Kangnam-gu, 135-942 Seoul (KR); Jeong-Ho Song, 705-33 Sinam 1-dong, Dong-gu, 701-822 Taegu (KR); Myung-Jin Lee, #101-407, Chunggiwa APT., 1525 Sinam 5-dong, Dong-gu, 701-768 Taegu (KR)

( * ) Notice: Subject to any disclaimer, the term of this patent is extended or adjusted under 35 U.S.C. 154(b) by 0 days.

(21) Appl. No.: 09/875,684

(22) Filed: Jun. 6, 2001

(65) Prior Publication Data

US 2002/0016475 A1 Feb. 7, 2002

(51) Int. Cl.[7] .......... C07F 17/02; C07D 35/02; C07C 5/02; B01J 31/00
(52) U.S. Cl. .......... 556/21; 556/23; 556/136; 585/250; 585/275; 548/303.7; 502/154; 502/155
(58) Field of Search .......... 556/21, 23, 136; 585/250, 275; 548/303.7; 502/154, 155

(56) References Cited

FOREIGN PATENT DOCUMENTS

| EP | 0 780 392 A1 | * | 12/1996 |
| JP | 61-151194 | * | 7/1986 |
| JP | 7-330776 | * | 12/1995 |

* cited by examiner

Primary Examiner—Porfirio Nazario-Gonzalez
(74) Attorney, Agent, or Firm—Frommer Lawrence & Haug LLP

(57) ABSTRACT

Ferrocenyldiphosphin-ruthenium complexes are new and good catalysts for the hydrogenation of exocyclic double bond of d-Thiophene 3 to d-Thiophane 4, both of which are intermediates of D-Biotin 1 synthesis.

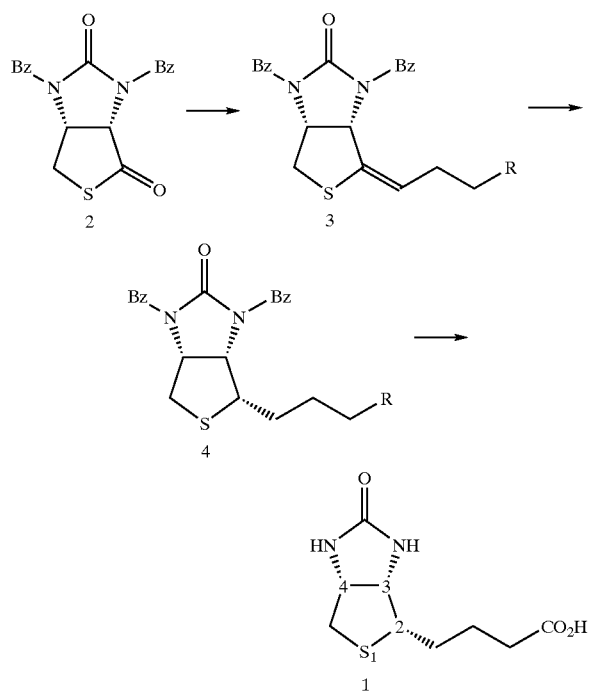

in which R signifies —$OCH_3$(3a), —$OCH_2CH_3$(3b), —$CH_2COOH$(3c), $CH_2COOCH_3$(3d) or —$CH_2COOEt$(3e) and Bz signifies benzyl group.

5 Claims, No Drawings

FERROCENYLDIPHOSPHINE-RUTHENIUM COMPLEXES AND A HYDROGENATION PROCESS OF EXOCYCLIC DOUBLE BOND OF D-THIOPHENE TO D-THIOPHANE

FIELD OF THE INVENTION

The present invention relates to new homogeneous ferrocenyldiphosphine-ruthenium complexes, good catalysts for the hydrogenation of d-thiophene to d-thiophane, and to a new process for the hydrogenation of d-thiophene 3 to d-thiophane 4 using ferrocenyldiphosphine-ruthenium complexes as catalysts.

BACKGROUND OF THE INVENTION

D-Biotin is one of the water-soluble B vitamins. It plays an essential role as a coenzyme in carboxylation reactions related to biochemical processes such as gluconeogenesis and fatty acid biosynthesis.

D-Biotin deficiency in poultry and swine causes a series of severe symptoms. These deficiencies are corrected by feeding Biotin as a feed additive. Hence, it is commercial importance.

Goldberg and Stembach's synthetic scheme, improved later by Gerecke etal, is regarded to be still one of the most efficient processes for the commercial production of natural-form D-Biotin. [U.S. Pat. No. 2,489,232, U.S. Pat. No. 2,489,235; U.S. Pat. No. 2,489,238; Helv. Chim. Acta, vol.53, 991(1970)].

The present invention relates to new homogeneous ferrocenyldiphosphine-ruthenium complexes, good catalysts for the hydrogenation of d-thiophene to d-thiophane, and to a new process for the hydrogenation of d-thiophene of the formula 3 to d-thiophane of the formula 4 using ferrocenyldiphosphine-ruthenium complexes as catalysts.

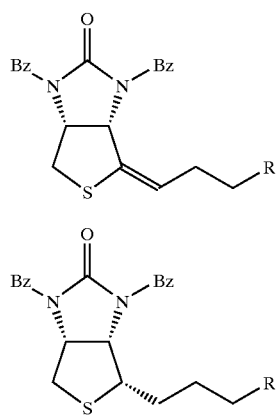

in which R signifies —OCH$_3$(3a), —OCH$_2$CH$_3$(3b), —CH$_2$COOH(3c), —CH$_2$COOCH$_3$(3d) or —CH$_2$COOEt (3e) and Bz signifies benzyl group.

d-Thiophene of the formular 3, which is derived from the reaction of d-Thiophene of the formula 2 with appropriate Grignard or Wittig reagents, is the intermediate of D-Biotin synthesis.

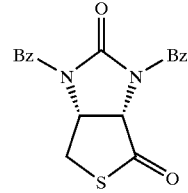

Up to present time, the conversion of d-Thiophene of the formula 3 to d-Thiophene of the formula 4 with the desired all-cis configuration at centers C-2, C-3, and C-4(see atom numbering on D-Biotin structure of the formula 1) is known to be accomplished by the catalytic hydrogenation using Palladium on carbon, Palladium hydroxide on carbon or Nickel catalyst, the heterogeneous catalysts.

However, many disadvantage are experienced with the uses of the heterogeneous catalysts. Palladium on carbon (dry form) is very expensive, air-sensitive and susceptible to sulfur poison. Palladium hydroxide on carbon is also expensive and sensitive to air. Nickel catalyst is less expensive but requires high pressure and high temperature for the hydrogenation of exocyclic double bond, which may not be adequate for the commercial application.

SUMMARY OF THE INVENTION

We found out new homogeneous catalysts for the hydrogenation of exocyclic double bond transforming d-thiophene of the formular 3 to d-thiophane of the formula 4, exhibiting the desired all-cis configuration at C-2, C-3 and C-4 centers. The homogeneous catalysts, we want to report herein, are new Ferrocenyldiphosphine-ruthenium complexes such as 1,1'-Bis(diphenylphosphino)-ferrocene-ruthenium complex, which compensate all disadvantages inheriting from the uses of known heterogeneous catalysts.

The above-mentioned new homogeneous catalysts which we invented are less expensive, less sensitive to air, easy to handle less susceptible to sulfur poison, and do not require high pressure and high temperature.

DETAILED DESCRIPTION OF THE INVENTION

Accordingly, the object of the present invention is to provide new homogeneous ferrocenyldiphosphine-ruthenium complexes which compensate all disadvantages of the known heterogeneous catalysts and which can replace existing heterogeneous catalysts such as Palladium and Nickel catalysts for the hydrogenation of exocyclic double bond of the d-thiophene of the formula 3.

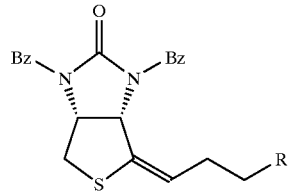

in which R signifies —OCH$_3$(3a), —OCH$_2$CH$_3$(3b), —CH$_2$COOH(3c), —CH$_2$COOCH$_3$(3d) or —CH$_2$COOEt (3e) and Bz signifies benzyl group.

Other object of the present invention is to provide a new method which utilizes the homogeneous catalysts for the hydrogenation of exocyclic double bond transforming d-thiophene of the formula 3 to d-thiophane of the formula 4, exhibiting the desired all-cis configuration at C-2, C-3 and C-4 centers.

The object of the present invention is achieved by providing a Ferrocenyldiphosphine-ruthenium complex selected from the group consisting of the complexes whose formulas are described as follow:

$RuCl_2(COD)_n$+PP in situ,      1.

$[RuCl_2(PP)]_2(NEt_3)$, and      2.

$RuHCl(PP)_2$      3.

wherein

COD signifies cyclooctadiene of the following formula,

and PP signifies a diphosphine ligand of the general formula

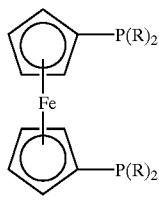

in which R is $C_1$–$C_{12}$ alkyl, $C_5$–$C_{12}$ cycloalkyl, $C_1$–$C_4$ alkyl or $C_1$–$C_4$ alkoxy-substituted, $C_5$–$C_{12}$ cycloalkyl, phenyl or phenyl which is substituted by 1 to 3 identical or different members selected from the group consisting of $C_1$–$C_4$, alkyl, $C_1$–$C_4$ alkoxy or halogen;

n is an integral number of 1–3 and the complexes of n=1, n=2 or n=3 exist together with one another.

In an economical view point, the most efficient catalyst, among all tested complexes, is {[1,1'-Bis(diphenylphosphino)ferrocene]dichlororuthenium(II)}2(triethylamine)[$RuCl_2(BPPF)]_2(NEt_3)$] complex whose ligand is known and can be prepared as described in J. J. Bishop etal, J. Organometal Chem. 1971, 27, 241.

Examples of suitable solvents of the reaction are aromatic hydrocarbons such as benzene or toluene, ethers such as diethyl ether, tetrahydrofuran or dioxane, chlorinated hydrocarbons such as dichloromethane or dichloroethane, alcohols such as methanol, ethanol or isopropyl alcohol, esters such as ethyl acetate or butyl acetate and mixtures of these solvents with one another. Preference is given to using methanol.

The addition of small amount of toluene to the substrate increases the hydrogenation rate, of which the amounts range from 1% to 50%, preferably 10%. However, the presence of water exhibits the opposite effect. The content of up to 0.1% water does not deteriorate the hydrogenation rate.

The hydrogenation is carried out at a temperature of from 20° C. to 150° C., preferably at 20° C. to 100° C., and at a pressure of from 1 kg/cm² to 200 kg/cm², preferably 10 to 30 kg/cm². The reaction time is 5 hours to 3 days, preferably 12–24 hours.

The comparative results of the hydrogenation of d-Thiophene 3 to d-Thiophane 4, with various Ferrocenyldiphophine-ruthenium complexes are shown in Table 1.

The Ferrocenyldiphosphine-ruthenium complex prepared in situ gives only the yield of 50%, however, the isolated complex, [$RuCl_2(BPPF)_2(NEt_3)$], (Entry 1) improves the yield to 85.1%. When the reaction conditions are optimized further, the yields are increased even higher, as shown in Table 2.

Analyses of the yield of 4a in the catalytic hydrogenation are conducted with the following instrument.

High-Performance Liquid Chromatography: SHIMADZU SCL-10A

Column: KROMASLI $C_8$

Solvent: Acetonitrile/Water(1:1 by volume) at a flow rate 1.5 ml/min.

EXAMPLE 1

Preparation of $RuHCl(BPPF)_2$ 2 g (7 mmol) of [$RuCl_2(COD)$]n (n=1–3), 8 g (14 mmol) of [1,1'-Bis(diphenylphosphino)ferrocene], 4.4 ml of triethylamine and 200 ml ethanol were introduced into a reactor and refluxed with heating for 6 hours under nitrogen atmosphere. After completion of the reaction, ethanol was distilled away, the residue was dissolved by adding 20 ml of dichlormethane and the insoluble portion was removed by filtration. Ether was gradually added to the filtrate to recrystallize. The crystals precipitated were filtered by filtration and dried in vacuo to obtain yellow solid.

EXAMPLE 2

Preparation of [$RuCl_2(BPPF)]_2(NEt_3)$

In a 250 ml Schlenk's tube were placed 2 g (7 mmol) of [$RuCl_2(COD)]_n$ (n=1–3) and 4 g (7 mmol) of BPPF. After sufficiently replacing the inside atmosphere of the tube with nitrogen, 4.2 ml of triethylamine and 40 ml of toluene were added thereto, and the resultant mixture was heated under reflux for 10 hours to perform reaction. After cooling the reaction mixture, the solid precipitated were separated by filtration and dried in vacuo obtain orange solid.

EXAMPLE 3

Production of d-Thiophane, 4a

In a 100 ml stainless steel autoclave, the inside atmosphere of which had previously been replaced with argon, were placed 13 g (33 mmol) of d-Thiophene, 3a, 25 ml of methanol, 1.25 ml of toulene and then, 0.0092 g (0.0034 mmol) of [$RuCl_2(COD)]_n$ (n=1–3) and 0.0183 g (0.0034 mmol) of BPPF was added in situ to the mixture to perform hydrogenation for 24 hours at a hydrogen pressure of 34 kg/cm² and at a reaction temperature of 100° C. Thereafter, the solvent was distilled off to obtain 6.53 g of d-Thiophane, 4a, The yield thereof was 50%.

EXAMPLE 4

Production of d-Thiophane, 4a

In a 100 ml stainless steel autoclave, the inside atmosphere of which had previously been replaced with argon, were placed 13 g (33 mmol) of d-Thiophene 3a, 25 ml of methanol, 1.25 ml of toluene and then, 0.041 g (0.0034 mmol) of RuHCl(BPPF)₂ prepared in Referential Example 1 was added to the mixture to perform hydrogen for 24 hours at a hydrogen pressure of 34 kg/cm² and at a reaction temperature of 100° C. Thereafter, the solvent was distilled off to provide 7.45 g of d-Thiophane, 4a. The yield thereof was 57%.

EXAMPLE 5

Production of d-Thiophane, 4a

In a 100 ml stainless steel autoclave, the inside atmosphere of which had previously been replaced with argon, were placed 13 g (33 mmol) of d-Thiophene, 3a 25 ml of methanol, 1.25 ml of toluene and then, 0.062 g (0.039 mmol) of [RuCl₂(BPPF)]₂(NEt₃) prepared in Referential Example 2 was added to the mixture to perform hydrogenation for 24 hours at a hydrogen pressure of 34 kg/cm² and at a reaction temperature of 100° C. Thereafter, the solvent was distilled off to provide 13.02 g of d-Thiophane, 4a, The yield thereof was 99.7%.

TABLE 1

Catalytic Hydrogenation of 3a with various Ru Complexes.[a]

| Entry | Catalyst | S/C ratio | Yield (%) |
|---|---|---|---|
| 1 | [RuCl₂(COD)]n + BPPF in situ | 1000 | 50.0 |
| 2 | RuHCl(BPPF)₂ | 1000 | 57.0 |
| 3 | [RuCl₂(BPPE)]₂(NEt₃) | 1000 | 85.1 |

[a]Reaction condition: same as Example 3.

TABLE 2

Catalytic Hydrogenation of 3a with [RuCl₂(BPPF)]₂(NEt₃).[a]

| Entry | Reaction Time (h) | T (° C.) | Toluene (%)[d] | Yield (%) |
|---|---|---|---|---|
| 1 | 24 | 60 | 0 | 78.4 |
| 2 | 24 | 120 | 0 | 67.8 |
| 3 | 24 | 100 | 0 | 85.1 |
| 4 | 48 | 100 | 0 | 85.4 |
| 5 | 72 | 100 | 0 | 88.4[b] |
| 6 | 24 | 100 | 5.0 | 86.6 |
| 7 | 24 | 100 | 8.0 | 91.8 |
| 8 | 24 | 100 | 12.0 | 92.8 |
| 9 | 24 | 100 | 12.0 | 99.7[c] |
| 10 | 24 | 100 | 25.0 | 45.4 |

[a]Reaction condition: same as Example 3; S/C ratio = 1000.
[b]After 48 h, 10% of catalyst more was added.
[c]S/C ratio = 850.
[d]The percentage of toluene to the substrate.

Up to the present time, the conversion of d-Thiophene to d-Thiophane is known to be accomplished by the catalytic hydrogenation using the heterogeneous catalysts such as Palladium on carbon, Palladium hydroxide on carbon or Nickel catalyst.

However, many disadvantage are experienced with the uses of the heterogeneous catalysts. These heterogeneous catalysts are very expensive, air-sensitive, susceptible to sulfur poison and require high pressure and high temperature.

As the present invention, catalytic hydrogenation is accomplished by using new homogeneous ferrocenyldiphosphine-ruthenium complexes which compensate all disadvantages inheriting from the uses of the above-mentioned heterogeneous catalysts.

What is claimed is:

1. A homogeneous Ferrocenyldiphosphine-ruthenium complex selected from the group consisting of the complexes whose formulas are described as follow:

RuCl₂(COD)ₙ+PP in situ,                       1.

[RuCl₂(PP)]₂(NEt₃) and                         2.

RuHCl(PP)₂                                      3.

wherein

COD signifies cyclooctadiene of the following formula,

and PP signifies a diphosphine ligand of the general formula

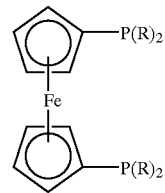

in which R is $C_1$–$C_{12}$ alkyl, $C_5$–$C_{12}$ cycloalkyl, $C_1$–$C_4$ alkyl or $C_1$–$C_4$ alkoxy-substituted, $C_5$–$C_{12}$ cycloalkyl, phenyl or phenyl which is substituted by identical or different members selected from the group consisting of $C_1$–$C_4$, alkyl, $C_1$–$C_4$ alkoxy or halogen;

n is an integral number of 1–3 and the complexes of n=1, n=2 or n=3 exist together with one another.

2. A process for the hydrogenation of exocyclic double bond d-thiophene of the formula 3 to d-thiophane of the formula 4,

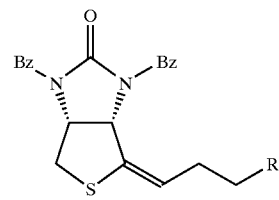

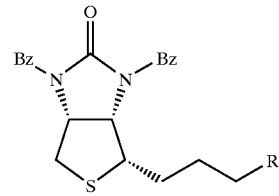

in which R signifies —OCH₃(3a), —OCH₂CH₃(3b), —CH₂COOH(3c), —CH₂COOCH₃(3d) or —CH₂COOEt (3e) and BZ signifies benzyl group;

by using a homogeneous Ferrocenyldiphosphine-ruthenium complex catalyst selected from the group consisting of the complexes whose formulas are described as follow:

RuCl₂(COD)n+PP in situ,                       1.

Ru₂Cl₄(PP)₂(NEt₃) and                          2.

RuHCl(PP)₂                                      3.

wherein

COD signifies cyclooctadiene of the following formula,

and PP signifies a diphosphine ligand of the general formula

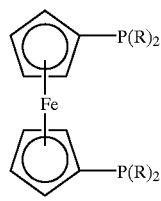

in which R is $C_1$–$C_{12}$ alkyl, $C_5$–$C_{12}$ cycloalkyl, $C_1$–$C_4$ alkyl or $C_1$–$C_4$ alkoxy-substituted, $C_5$–$C_{12}$ cycloalkyl, phenyl or phenyl which is substituted by identical or different members selected from the group consisting of $C_1$–$C_4$, alkyl, $C_1$–$C_4$ alkoxy or halogen;

n is an integral number of 1–3 and the complexes of n=, n=2 or n=3 exist together with one another.

3. The process of claim 2 wherein the hydrogenation reaction is carried out in an organic solvent selected from the group consisting of aromatic hydrocarbon (e.g. benzen or toluene), straight ether (e.g. dimethyl ether or diethyl ether), cyclic ether (e.g. tetrahydrofuran or dioxane), chlorinated hydrocarbon (e.g. dichloromethane or dichloroethane), alcohol (e.g. methanol, ethanol or isopropyl alcohol), ester (e.g. ethyl acetate or butyl acetate) or mixture thereof.

4. The process of claim 2 wherein the hydrogenation reaction is carried out in a mixed solvent of an aromatic hydrocarbon (e.g. benzene or toluene) with another organic solvent selected from the group consisting of straight ether (e.g. dimethyl ether or diethyl ether), cyclic ether (e.g. tetrahydrofuran or dioxane), chlorinated hydrocarbon (e.g. dichloromethane or dichloroethane), alcohol (e.g. methanol, ethanol or isopropyl alcohol) ester (e.g. ethyl acetate or butyl acetate).

5. The process of claim 2 wherein the hydrogenation reaction is carried out in the mixed solvent toluene and methanol.

* * * * *